(12) United States Patent
Soper et al.

(10) Patent No.: US 11,864,856 B2
(45) Date of Patent: *Jan. 9, 2024

(54) SYSTEMS AND METHODS OF CONTINUOUS REGISTRATION FOR IMAGE-GUIDED SURGERY

(71) Applicant: INTUITIVE SURGICAL OPERATIONS, INC., Sunnyvale, CA (US)

(72) Inventors: Timothy D. Soper, San Jose, CA (US); Vincent Duindam, San Francisco, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/154,710

(22) Filed: Jan. 13, 2023

(65) Prior Publication Data

US 2023/0149108 A1    May 18, 2023

Related U.S. Application Data

(63) Continuation of application No. 17/353,322, filed on Jun. 21, 2021, now Pat. No. 11,583,353, which is a
(Continued)

(51) Int. Cl.
*A61B 34/20*    (2016.01)
*A61B 34/37*    (2016.01)
(Continued)

(52) U.S. Cl.
CPC ........ *A61B 34/37* (2016.02); *A61B 1/000094* (2022.02); *A61B 1/00147* (2013.01);
(Continued)

(58) Field of Classification Search
CPC ............. A61B 34/37; A61B 1/000094; A61B 1/00147; A61B 34/10; A61B 34/20;
(Continued)

(56) References Cited

U.S. PATENT DOCUMENTS 6,380,732 B1    4/2002  Gilboa
6,389,187 B1    5/2002  Greenaway et al.
(Continued)

FOREIGN PATENT DOCUMENTS

EP    1504713 A1    2/2005
EP    2536325 B1    10/2015
(Continued)

OTHER PUBLICATIONS

Extended European Search Report for Application No. EP17868421.3 dated May 8, 2020, 12 pages.
(Continued)

*Primary Examiner* — Siamak Harandi
(74) *Attorney, Agent, or Firm* — Haynes & Boone, LLP

(57) ABSTRACT

Methods and systems of registering a model of one or more anatomic passageways of a patient to a patient space are provided herein. An exemplary method may include accessing a set of model points of the model of the passageways, the model points being associated with a model space, collecting measured points along a length of a catheter inserted into the passageways of the patient, the measured points determined by a shape of the catheter, and assigning points of the first set to a plurality of subsets. The exemplary method may further include registering each of the subsets with the model points to produce a plurality of registration candidates, comparing the candidates to identify an optimal subset associated with an optimal registration of the plurality
(Continued)

of candidates that translates the set of model points and at least one set of the sets of measured points into a common space.

20 Claims, 16 Drawing Sheets

Related U.S. Application Data continuation of application No. 16/343,093, filed as application No. PCT/US2017/059358 on Oct. 31, 2017, now Pat. No. 11,065,059.

(60) Provisional application No. 62/416,393, filed on Nov. 2, 2016.

(51) Int. Cl.
    *A61B 34/10*     (2016.01)
    *G06T 7/33*     (2017.01)
    *G06F 30/23*     (2020.01)
    *G06T 3/00*     (2006.01)
    *G06T 17/20*     (2006.01)
    *A61B 1/00*     (2006.01)

(52) U.S. Cl.
    CPC .............. *A61B 34/10* (2016.02); *A61B 34/20* (2016.02); *G06F 30/23* (2020.01); *G06T 3/0068* (2013.01); *G06T 7/344* (2017.01); *G06T 17/20* (2013.01); *A61B 2034/105* (2016.02); *A61B 2034/2065* (2016.02); *G06T 2210/41* (2013.01)

(58) Field of Classification Search
    CPC ...... A61B 2034/105; A61B 2034/2065; A61B 1/0051; A61B 1/2676; A61B 2017/00699; A61B 2034/2051; A61B 2034/2055; A61B 2034/2059; A61B 2034/2061; A61B 2034/301; A61B 2090/364; A61B 90/37; A61B 2034/102; A61B 2034/2046; A61B 90/36; G06F 30/23; G06T 3/0068; G06T 7/344; G06T 17/20; G06T 2210/41; A61M 25/0113; A61M 2025/0166; A61M 25/01; A61M 25/0105; A61M 2205/502
See application file for complete search history.

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 8,611,983 B2 * | 12/2013 | Glossop ............ | A61M 25/0136 600/414 |
| 8,900,131 B2 | 12/2014 | Chopra et al. | |
| 9,259,274 B2 | 2/2016 | Prisco | |
| 9,452,276 B2 | 9/2016 | Duindam et al. | |
| 11,065,059 B2 | 7/2021 | Soper et al. | |
| 11,583,353 B2 | 2/2023 | Soper et al. | |
| 2006/0013523 A1 | 1/2006 | Childlers et al. | |
| 2008/0118135 A1 | 5/2008 | Averbuch et al. | |
| 2009/0156951 A1 | 6/2009 | Averbuch | |
| 2011/0116693 A1 | 5/2011 | Li et al. | |
| 2011/0282151 A1 | 11/2011 | Trovato et al. | |
| 2012/0046521 A1 | 2/2012 | Hunter et al. | |
| 2012/0059248 A1 | 3/2012 | Holsing et al. | |
| 2012/0203067 A1 | 8/2012 | Higgins et al. | |
| 2012/0302878 A1 | 11/2012 | Liu et al. | |
| 2013/0223702 A1 | 8/2013 | Holsing et al. | |
| 2014/0051986 A1 | 2/2014 | Zhao et al. | |
| 2015/0265368 A1 | 9/2015 | Chopra et al. | |
| 2016/0000356 A1 | 1/2016 | Brown et al. | |
| 2020/0046431 A1 | 2/2020 | Soper et al. | |
| 2021/0307837 A1 | 10/2021 | Soper et al. | |

FOREIGN PATENT DOCUMENTS

| | | | |
|---|---|---|---|
| EP | 3058889 A1 | 8/2016 | |
| JP | 2007519443 A | 7/2007 | |
| WO | WO-2009147683 A1 | 12/2009 | |
| WO | WO-2014028394 A1 | 2/2014 | |
| WO | WO-2016018646 A1 | 2/2016 | |
| WO | WO-2016025465 A1 | 2/2016 | |
| WO | WO-2016164311 A1 | 10/2016 | |
| WO | WO-2017030913 A2 | 2/2017 | |

OTHER PUBLICATIONS

International Preliminary Report on Patentability for Application No. PCT/US2017/059358, dated May 16, 2019, 7 pages (ISRG08550/PCT).

International Search Report and Written Opinion for Application No. PCT/US2017/059358, dated Jan. 14, 2018, 10 pages (ISRG08550/PCT).

Vertut, J, and Coiffet, P., "Robot Technology: Teleoperation and Robotics Evolution and Development," English translation, Prentice Hall, Inc., Inglewood Cliffs, NJ, USA 1986, vol. 3A, 332 pages.

* cited by examiner

+ - Points at $t_1$
● - Points at $t_2$
× - Points at $t_3$
○ - Points at $t_4$

SYSTEMS AND METHODS OF CONTINUOUS REGISTRATION FOR IMAGE-GUIDED SURGERY

RELATED APPLICATIONS

This patent application is a continuation of U.S. patent application Ser. No. 17/353,322, filed Jun. 21, 2021 which is a continuation of U.S. patent application Ser. No. 16/343,093, filed Apr. 18, 2019 which is the U.S. national phase of International Application No. PCT/US2017/059358, filed Oct. 31, 2017, which designated the U.S. and claims priority to and the benefit of the filing date of U.S. Provisional Patent Application 62/416,393, entitled "Systems and Methods of Continuous Registration For Image-Guided Surgery," filed Nov. 2, 2016, which is are incorporated by reference herein in its their entirety.

FIELD

The present disclosure is directed to systems and methods for conducting an image-guided procedure, and more particularly to systems and methods for registering a model of patient anatomy to one or more instruments being used in a medical procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Systems and methods for performing registered models for use during image-guided surgery with minimal clinical disturbances are needed.

SUMMARY

The embodiments of the invention are best summarized by the claims that follow the description.

However, an exemplary method of registering a model of one or more anatomic passageways of a patient to a patient space may include accessing a set of model points in a model space of the model of one or more anatomic passageways of the patient, collecting a first set of measured points along a length of a catheter inserted into the one or more anatomic passageways of the patient, the measured points determined by a shape of the catheter in the patient space, and assigning points of the first set of measured points to a plurality of first subsets of measured points. The exemplary method may further include registering the first subsets of measured points with the set of model points to produce a first plurality of registration candidates, comparing the registration candidates to identify an optimal subset associated with an optimal registration of the first plurality of registration candidates, and displaying a visual representation of the optimal registration in a user interface provided by a display. The optimal registration translates the set of model points and at least one subset of the first set of measured points into a common space.

Another exemplary method of registering a model of one or more anatomic passageways of a patient to a patient space, may include accessing a set of model points of the model of one or more anatomic passageways of a patient, collecting a set of measured points along a length of a catheter inserted into the one or more anatomic passageways of the patient, the measured points determined by a shape of the catheter in the patient space, and registering subsets of the set of measured points with the set of model points to produce a plurality of registration candidates. The exemplary method may further include selecting a registration candidate of the plurality of registration candidates for use in performing a medical procedure and applying the selected registration candidate to the set of model points of the model to register the model to the patient space.

An exemplary medical imaging system may include a movement detector, a flexible catheter having a proximal end coupled to an instrument carriage that is moveable along an insertion stage, and a point gathering instrument extending along a length of the flexible catheter. The exemplary system may further include a tracking system that is configured to register a set of measured points collected by the point gathering instrument to a model of one or more anatomic passageways. The tracking system may access a set of model points in a model space and collect the set of measured points along the length of the flexible catheter inserted into the one or more anatomic passageways of a patient, the measured points being determined by a shape of the catheter in a patient space. The tracking system may also assign the set of measured points into subsets according to a periodic physiological function monitored by the movement detector, select a first registration candidate from a plurality of registration candidates based on the subsets of measured points, and apply the selected first registration candidate to the set of model points of the model to register the model to the patient space. It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 2A:
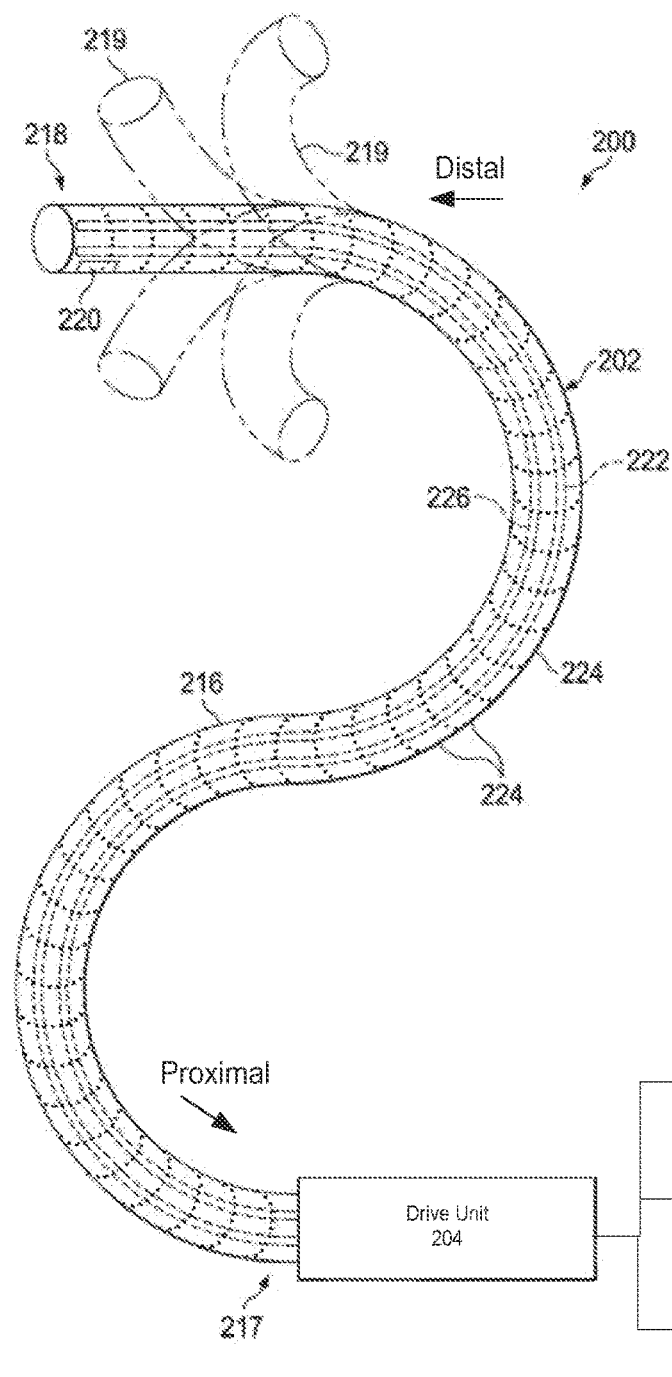
FIG. 2A is a simplified diagram of a medical instrument system utilizing aspects of the present disclosure.
Figure 2B:
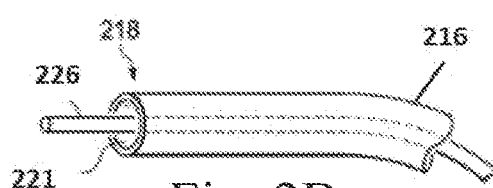
FIG. 2B is a simplified diagram of a medical instrument with an extended medical tool according to some embodiments.
Figure 3A:
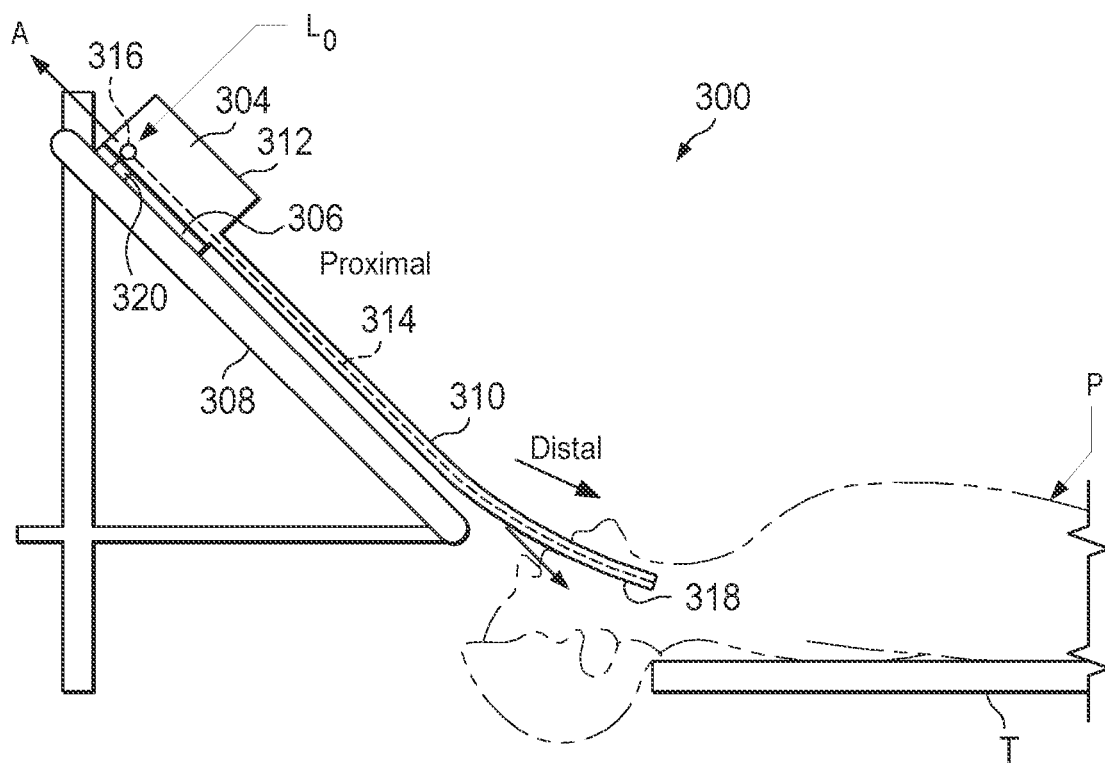
FIGS. 3A and 3B are side views of a patient coordinate space including a medical instrument mounted on an insertion assembly according to some embodiments of the present disclosure.
Figure 3B:
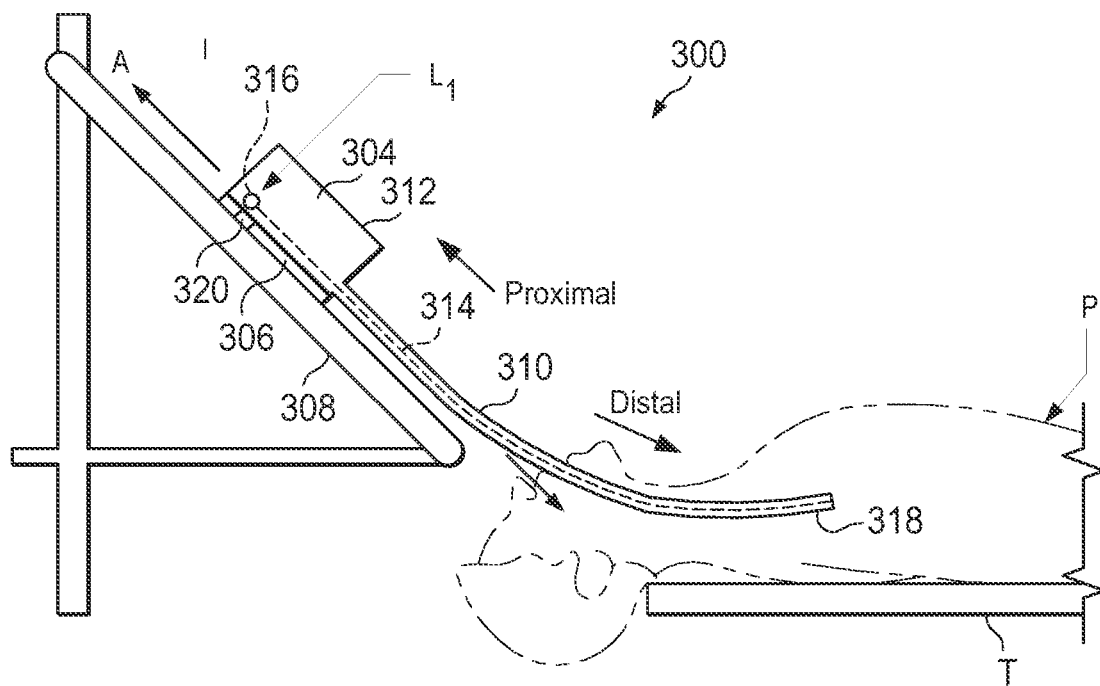
Figure 4A:
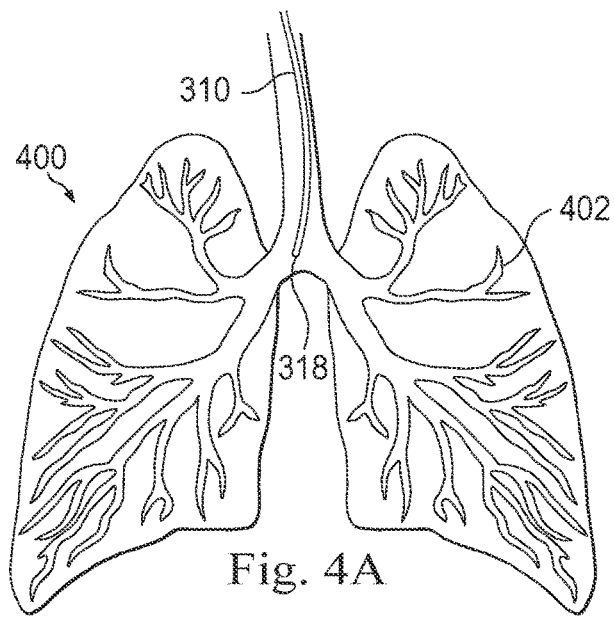
Figure 4B:
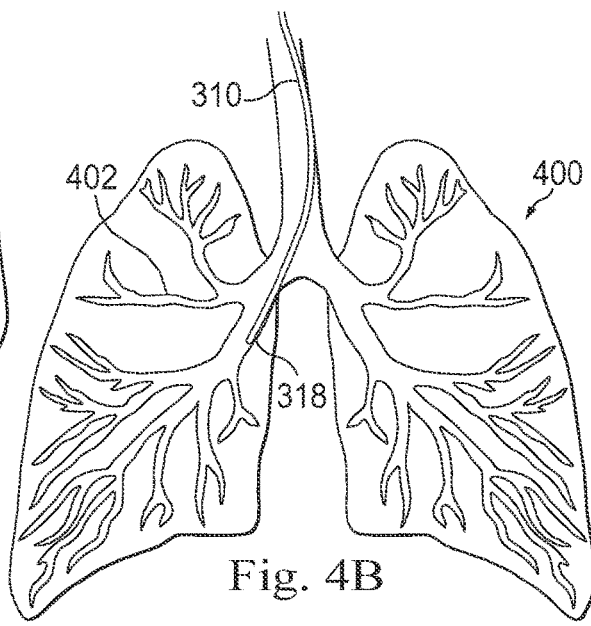
Figure 4C:
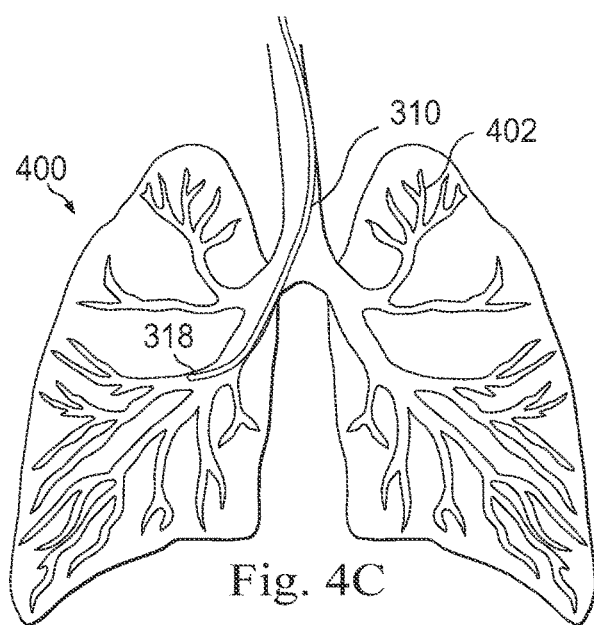
Figure 4D:
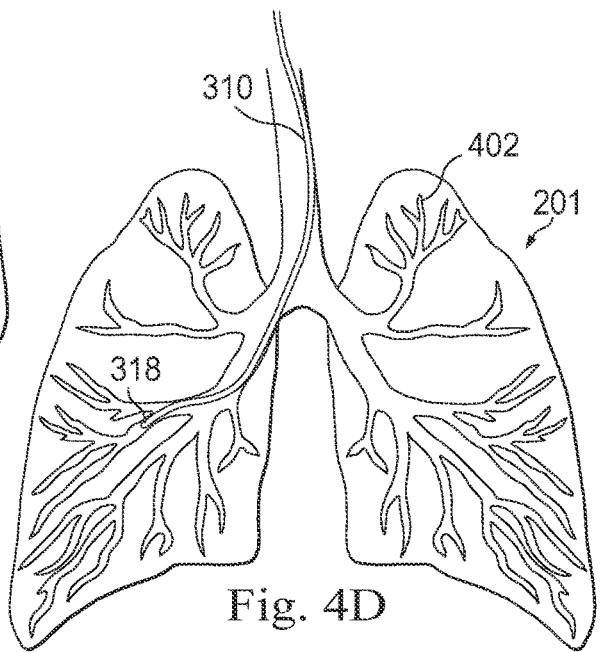

FIGS. 4A, 4B, 4C, and 4D illustrates the distal end of the medical instrument system of FIGS. 2, 3A, 3B, during insertion within a human lung.

Figure 5:
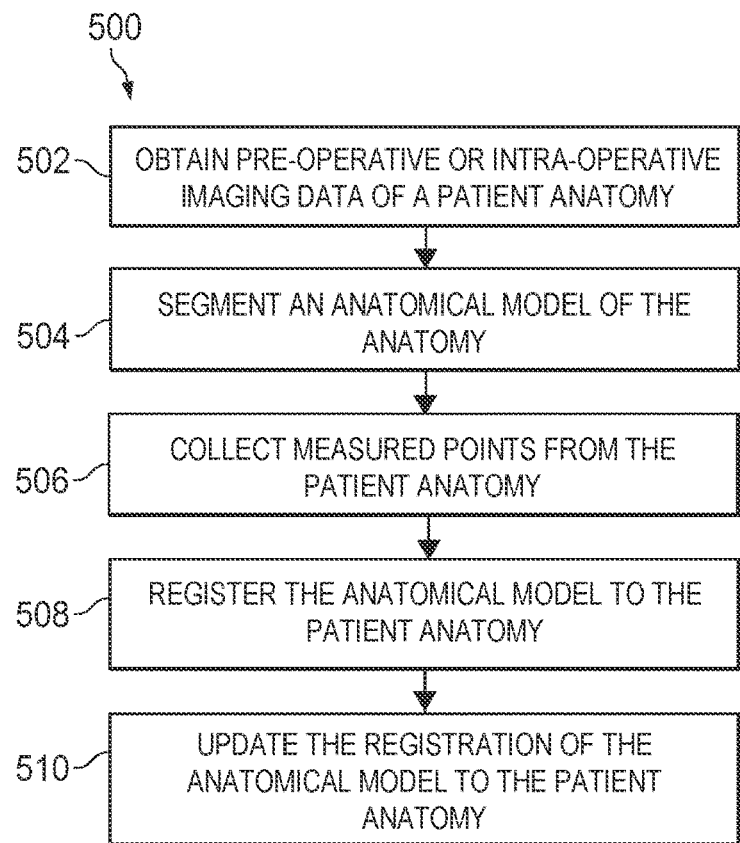

FIG. 5 is a flowchart illustrating a method used to provide guidance in an image-guided surgical procedure according to an embodiment of the present disclosure.

Figure 6A:
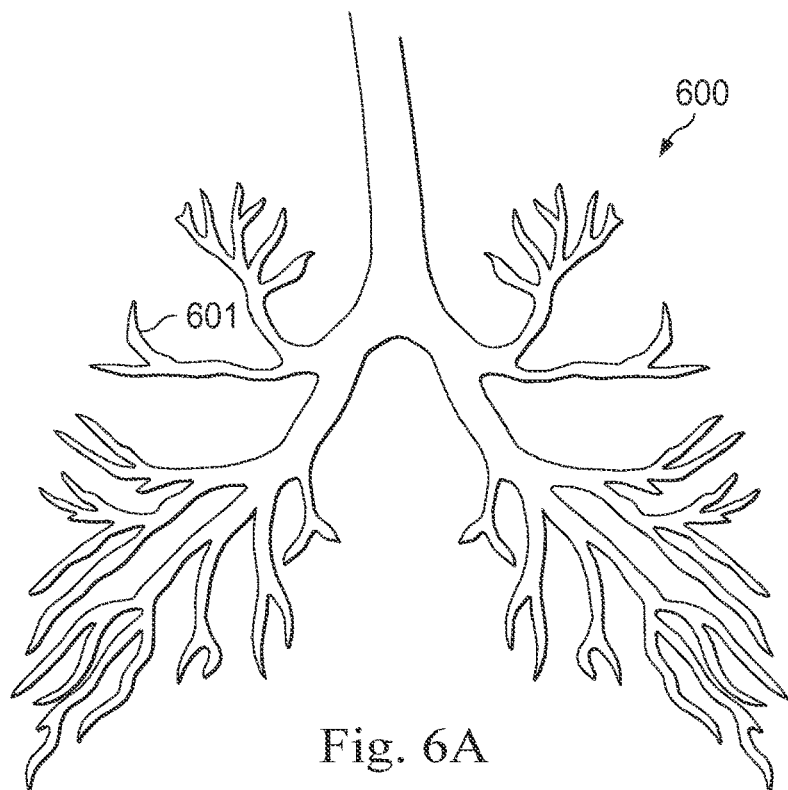
Figure 6B:
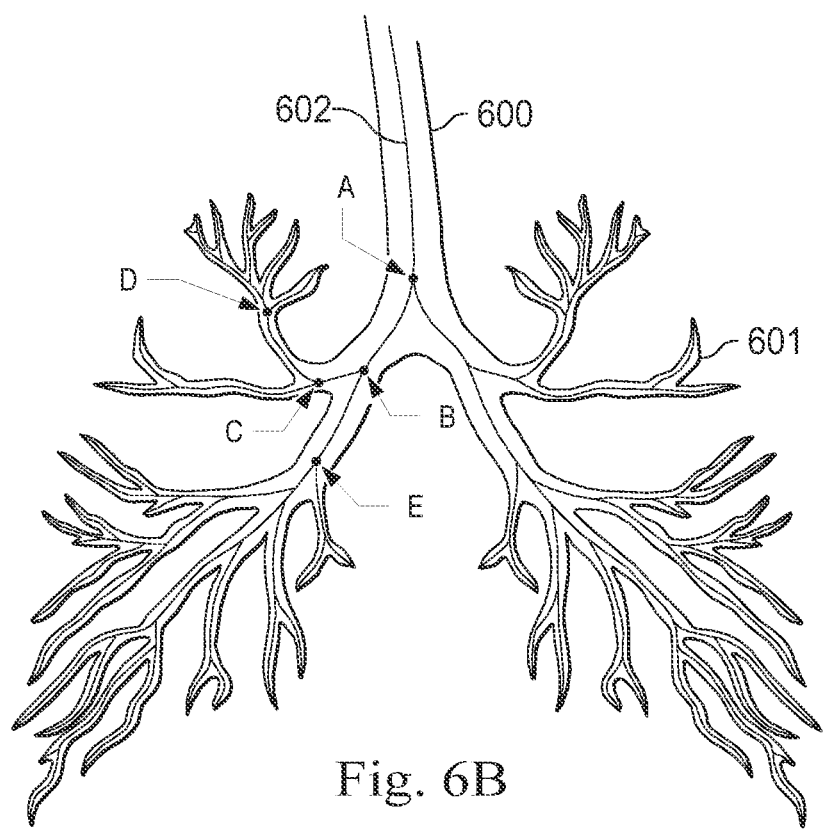
Figure 6C:
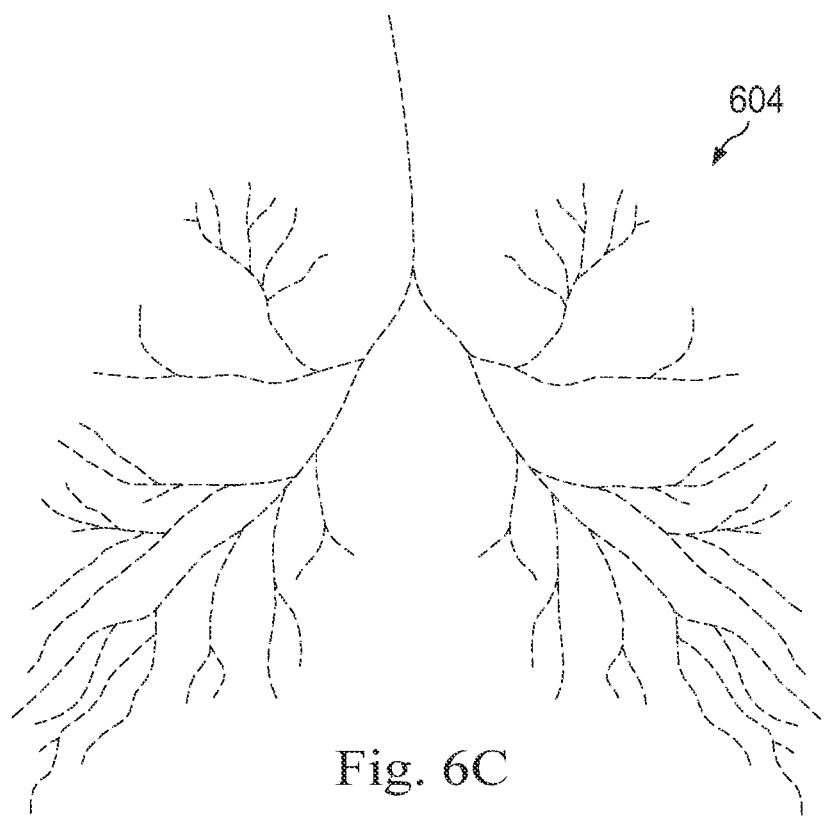

FIGS. 6A, 6B, and 6C illustrate steps in segmentation process that generates a model of a human lung for registration according to an embodiment of the present disclosure.

Figure 7:
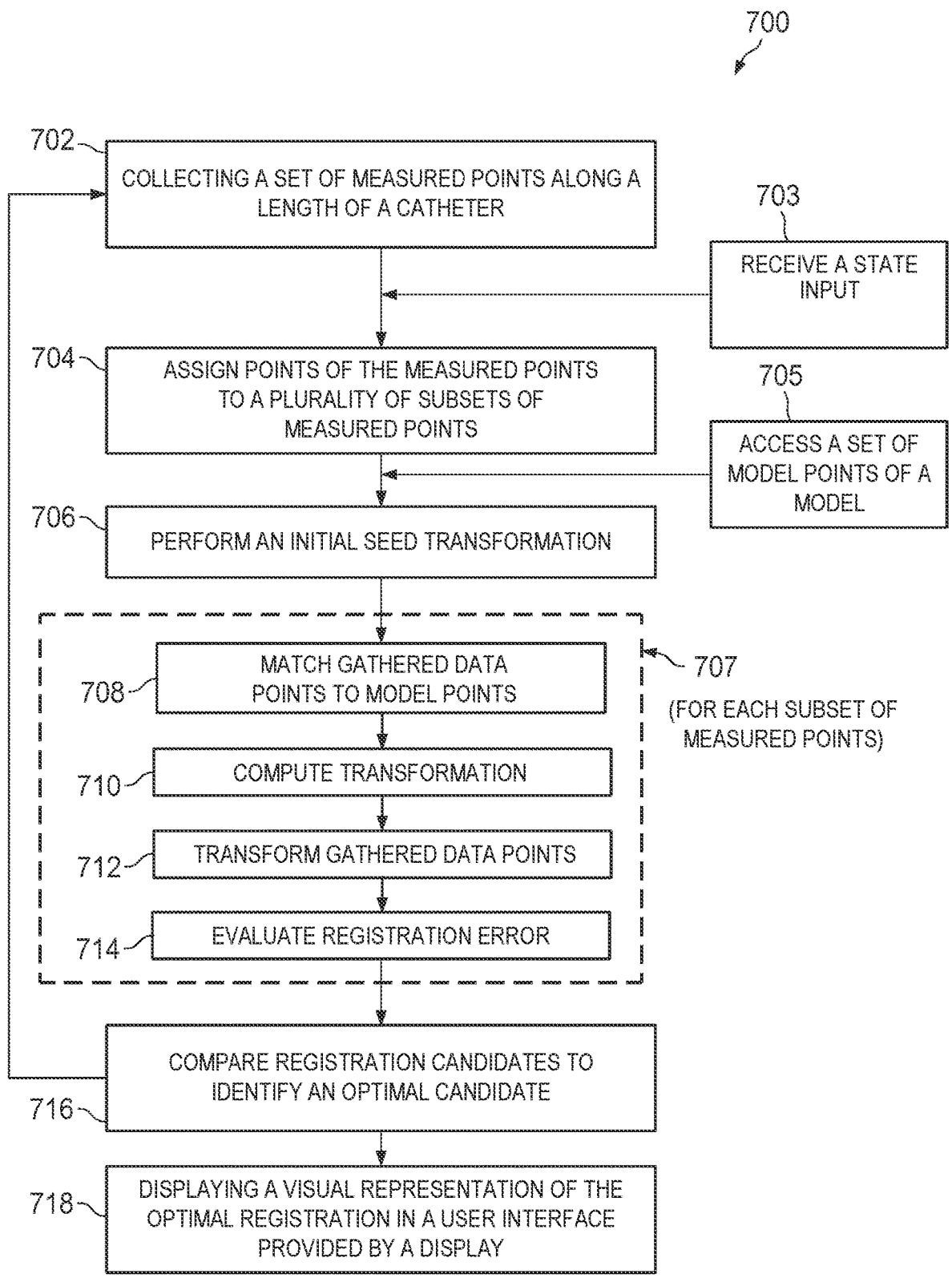

FIG. 7 illustrates a flowchart of a portion of an image-guided surgical procedure according to an embodiment of the present disclosure.

Figure 8A:
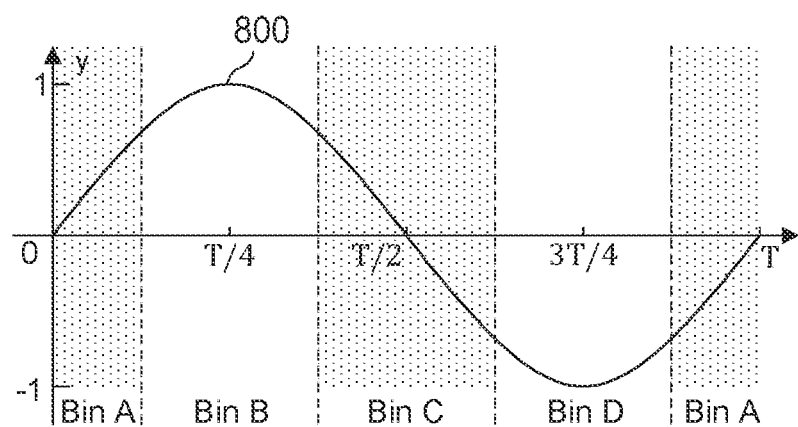
Figure 8B:
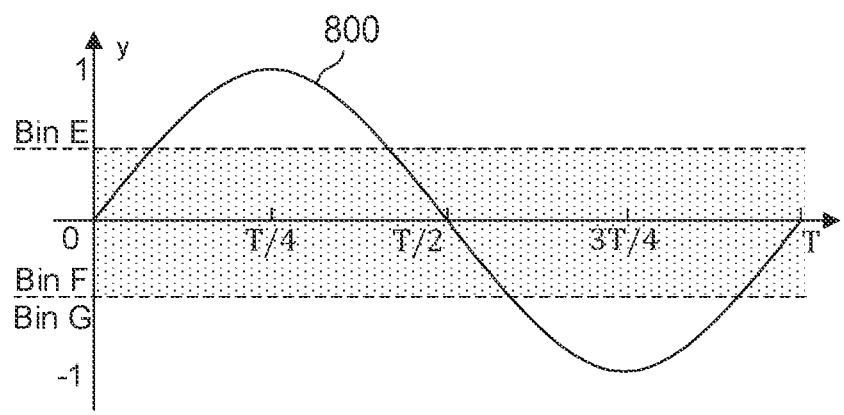

FIGS. 8A and 8B illustrate a phase-based binning process and an amplitude-based binning process for collecting measured points within patient anatomy according to an embodiment of the present disclosure.

Figure 9:
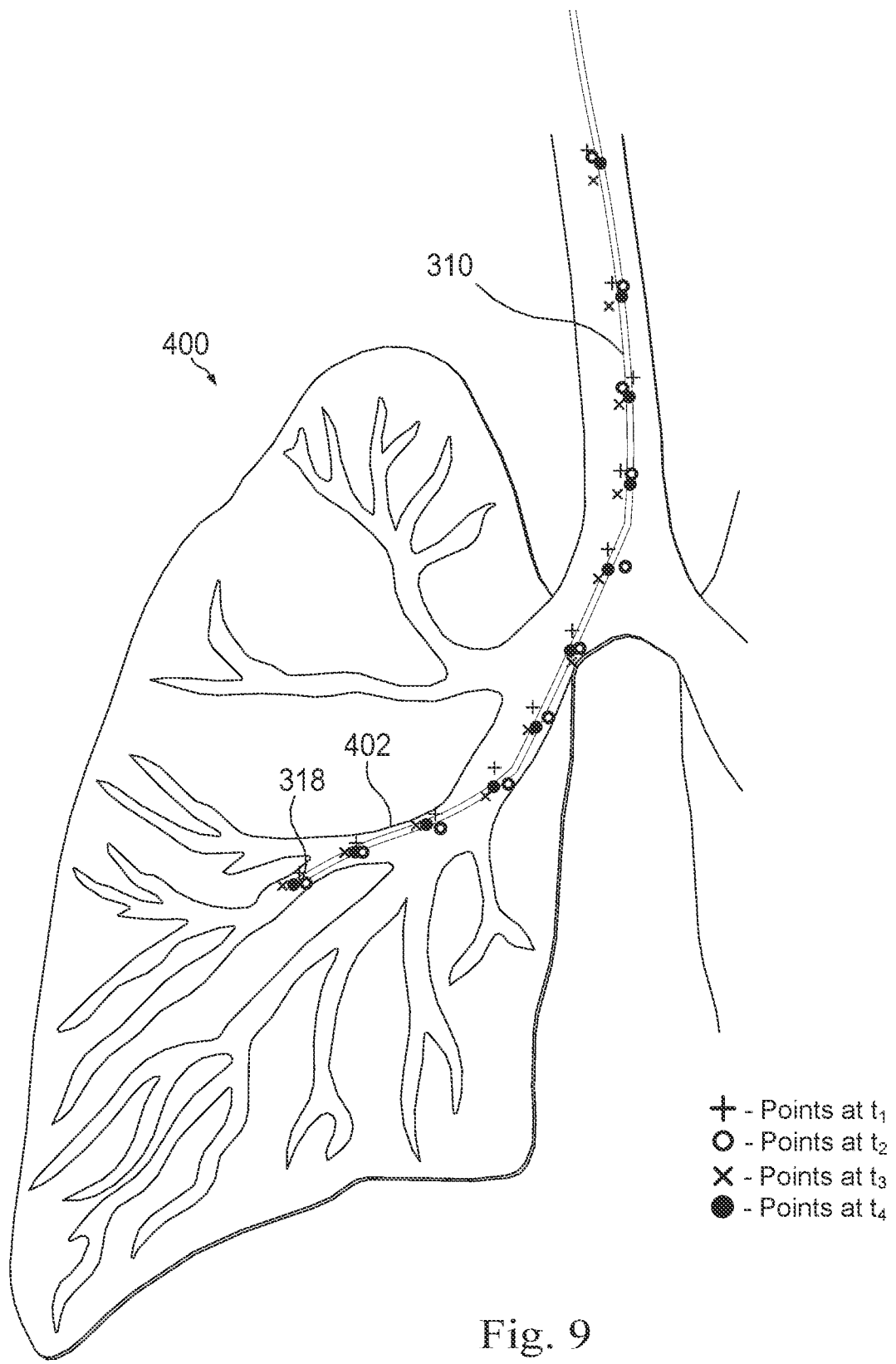

FIG. 9 illustrates phase-based and amplitude-based binning of measured points within patient anatomy according to an embodiment of the present disclosure.

FIGS. 10A, 10B, 10C, and 10D illustrate insertion depth-based binning of measured points within patient anatomy according to an embodiment of the present disclosure.

Figure 11A:
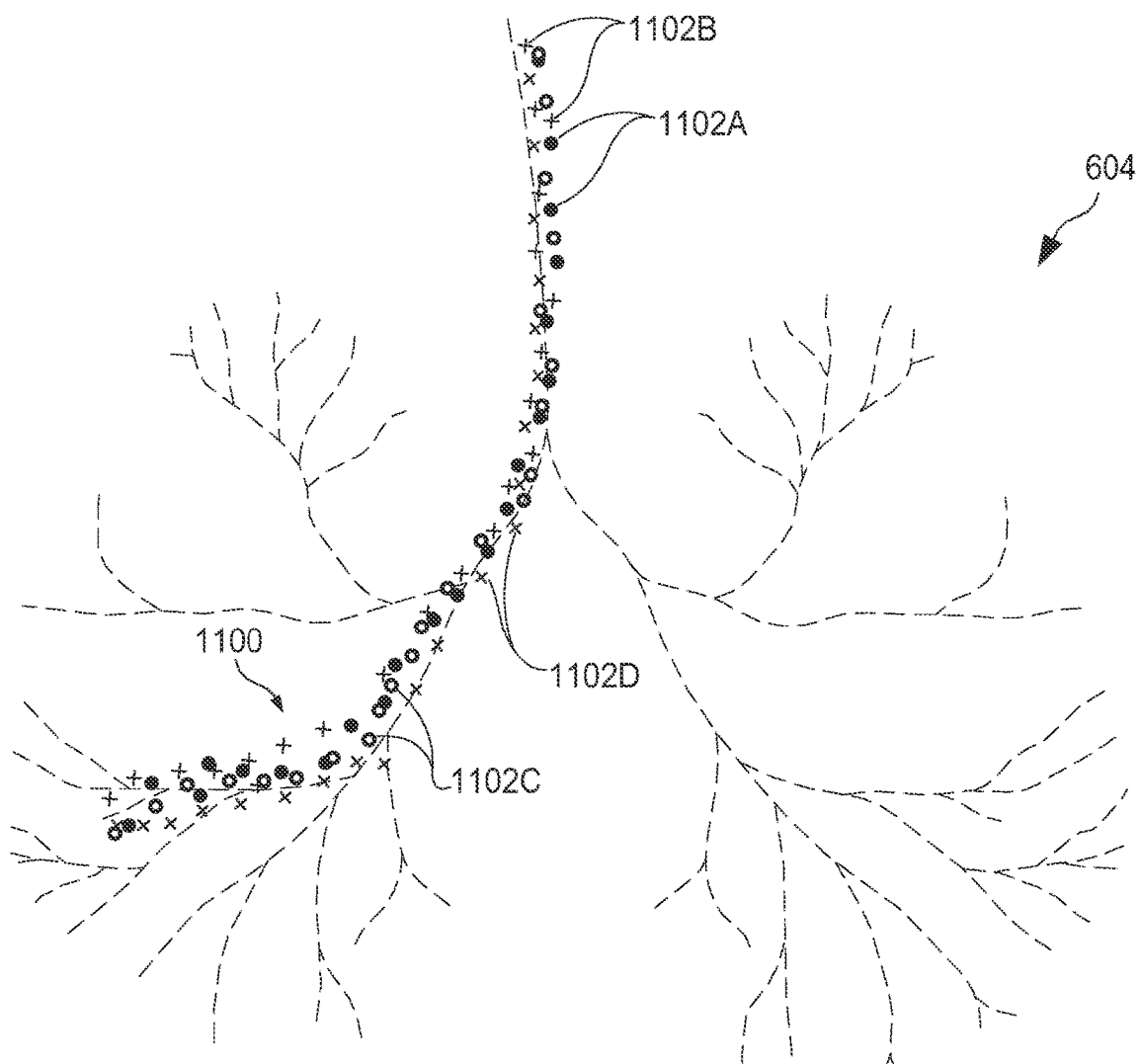
Figure 11B:
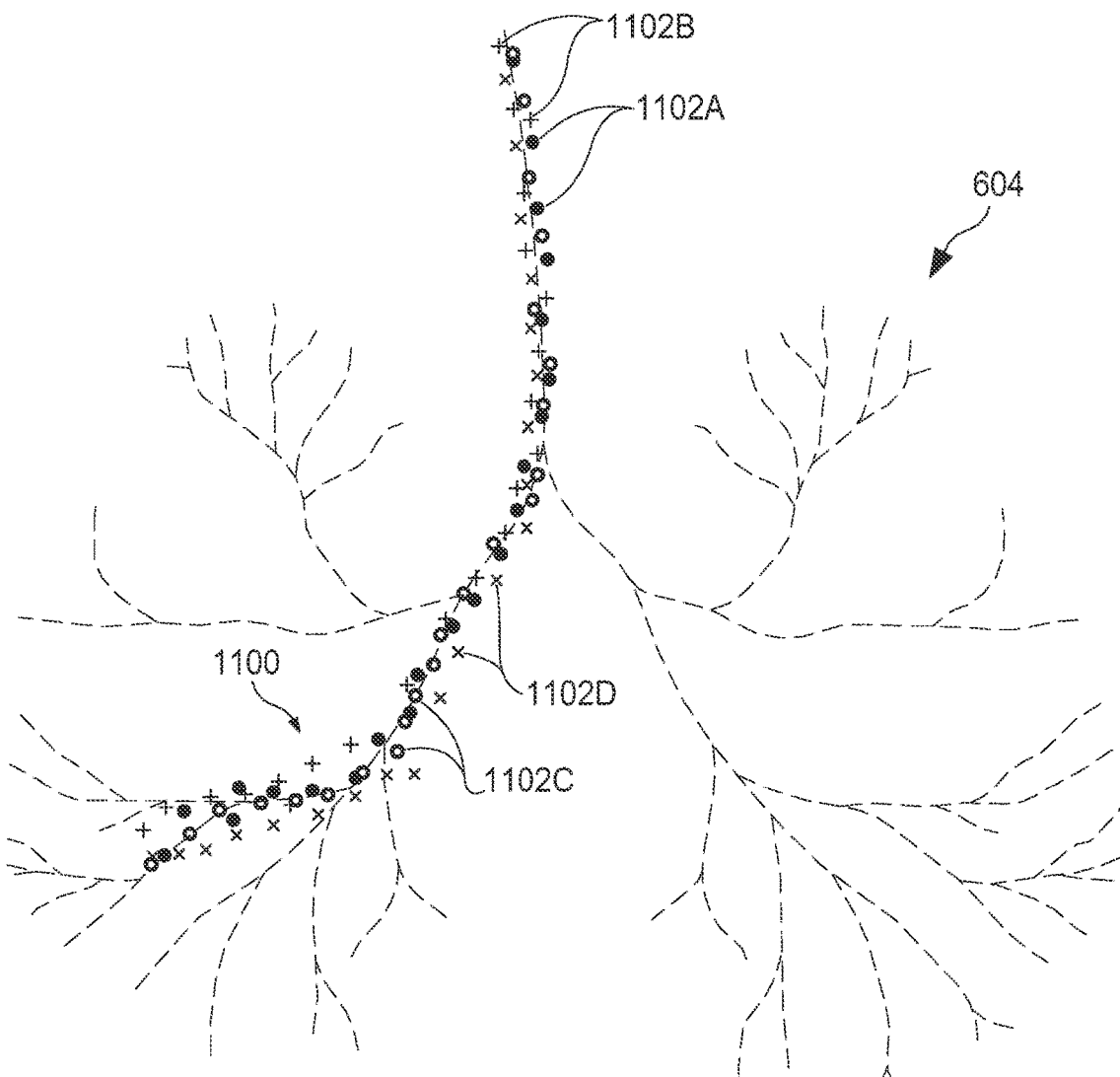

FIGS. 11A and 11B illustrate registration between a centerline model of patient anatomy and a set of measured points according to an embodiment of the present disclosure.

Figure 12A:
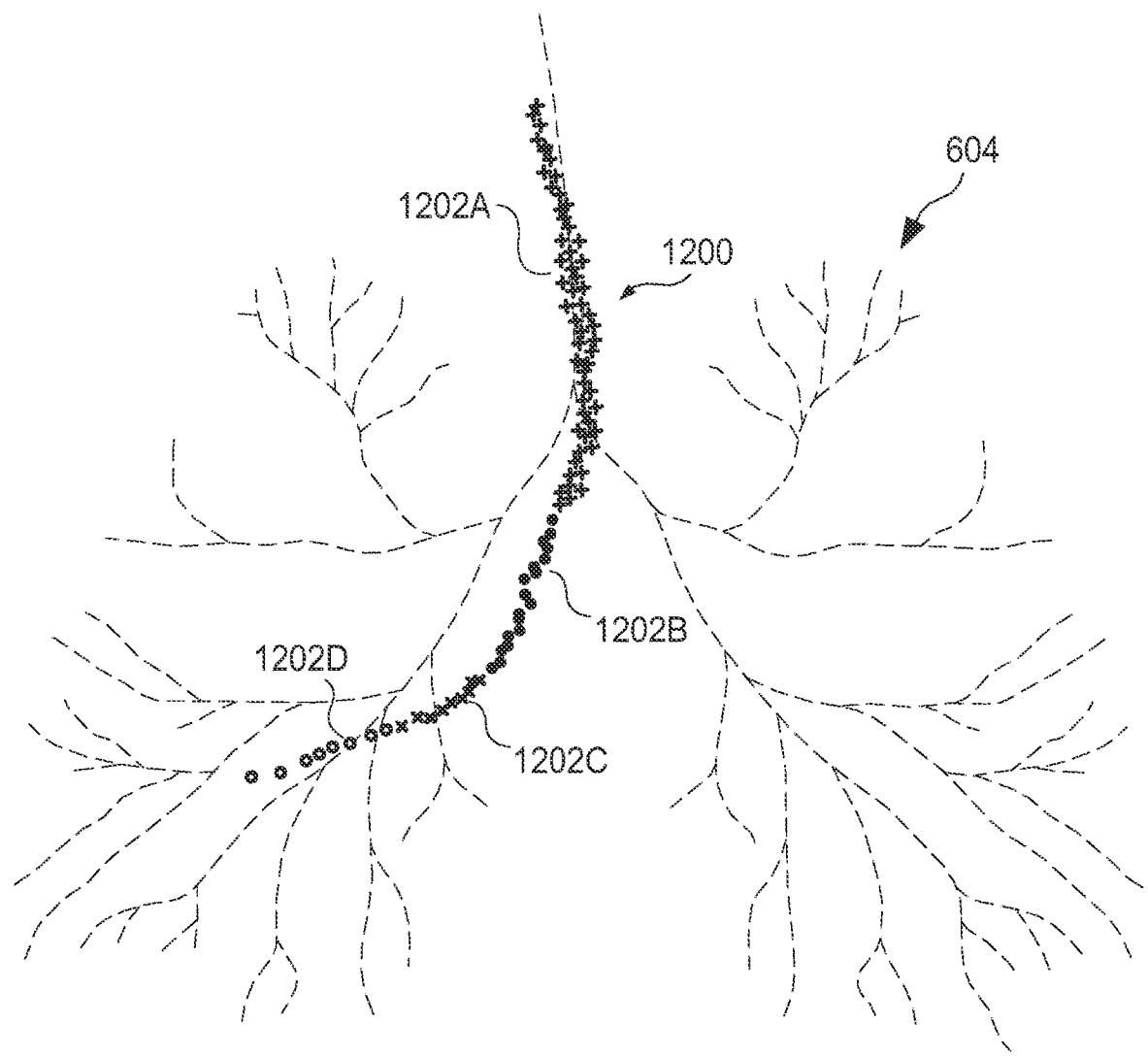
Figure 12B:
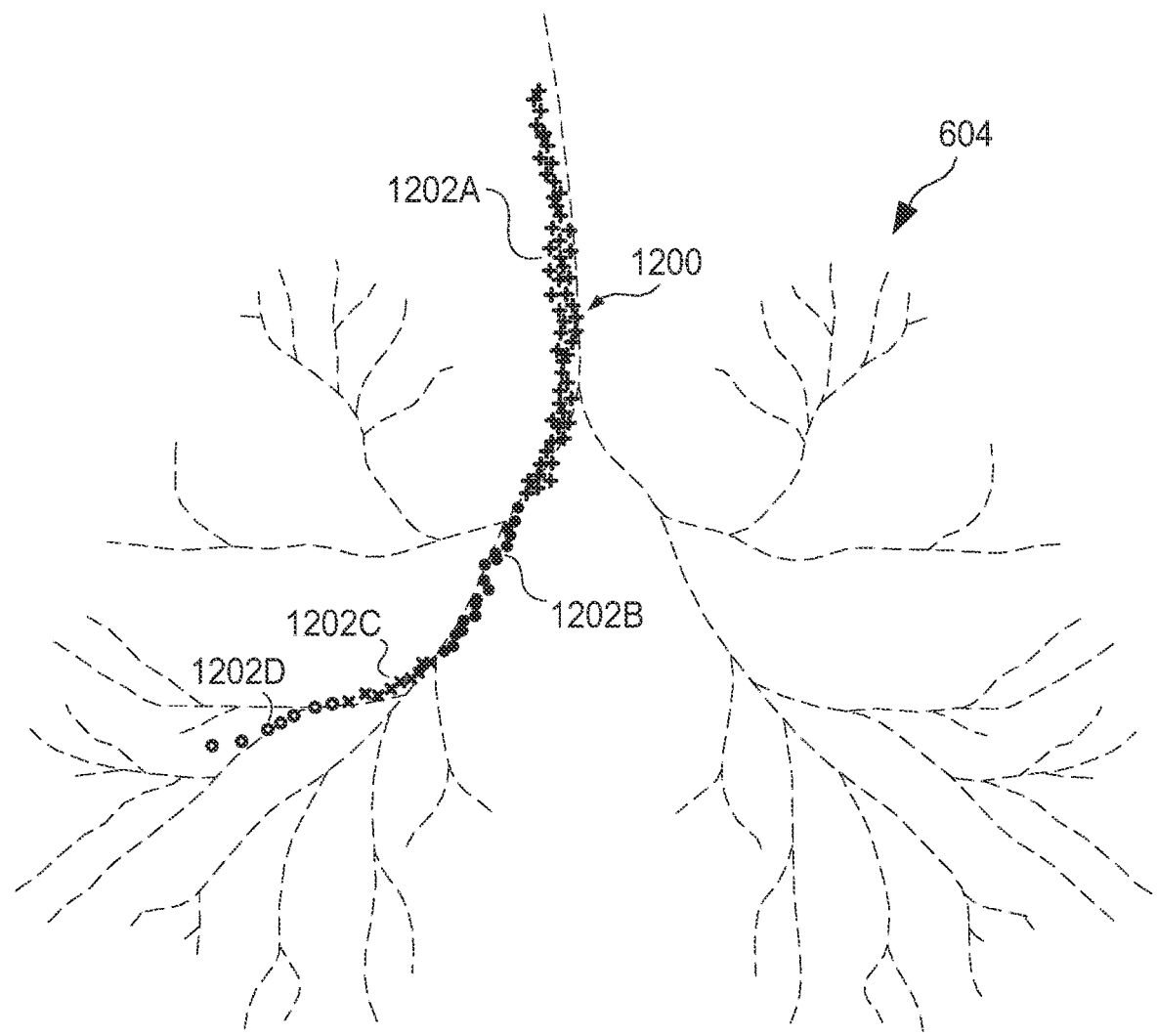

FIGS. 12A and 12B illustrate registration between a centerline model of patient anatomy and a set of measured points according to another embodiment of the present disclosure.

Figure 13A:
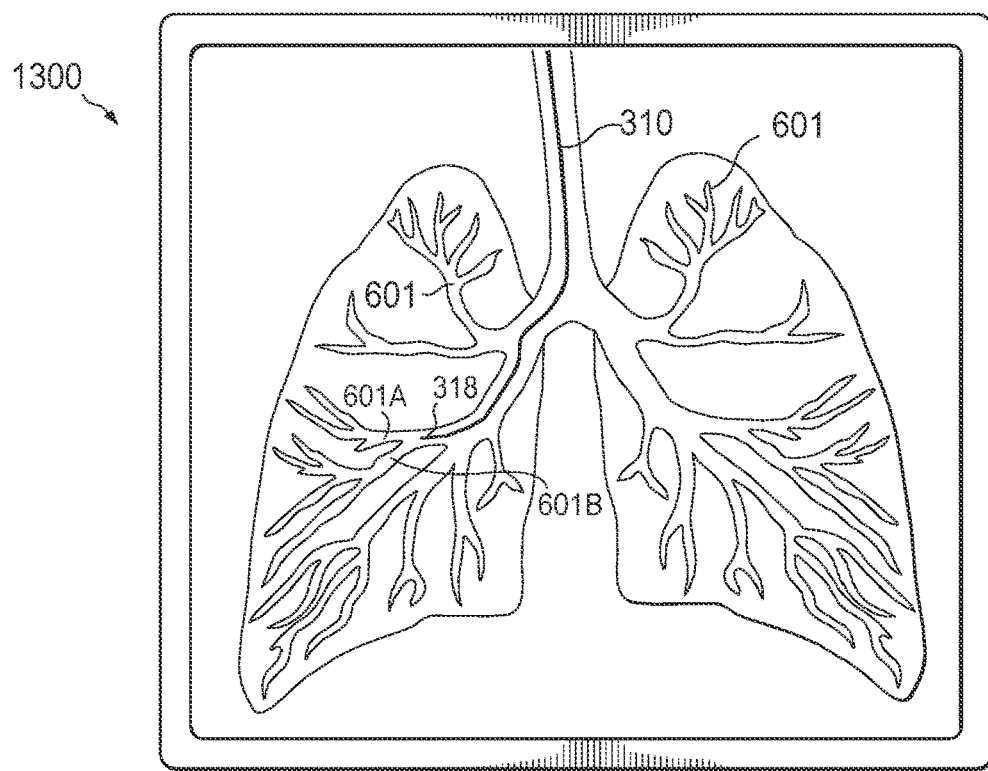
Figure 13B:
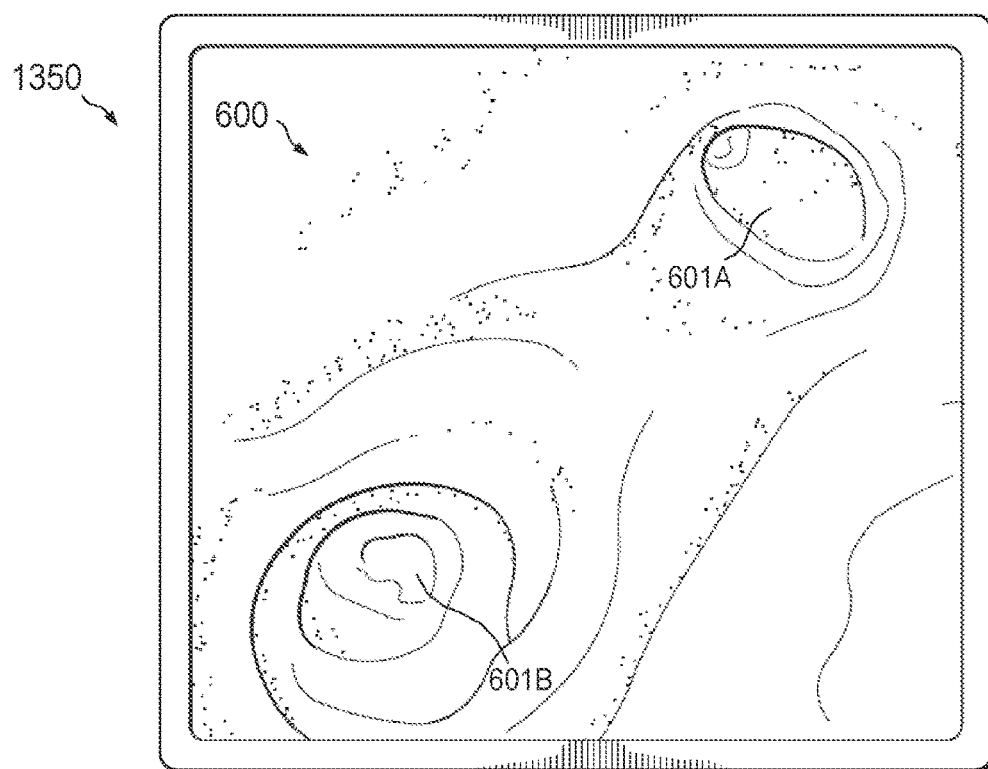

FIGS. 13A and 13B illustrates a display stage of a registration technique according to an embodiment of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
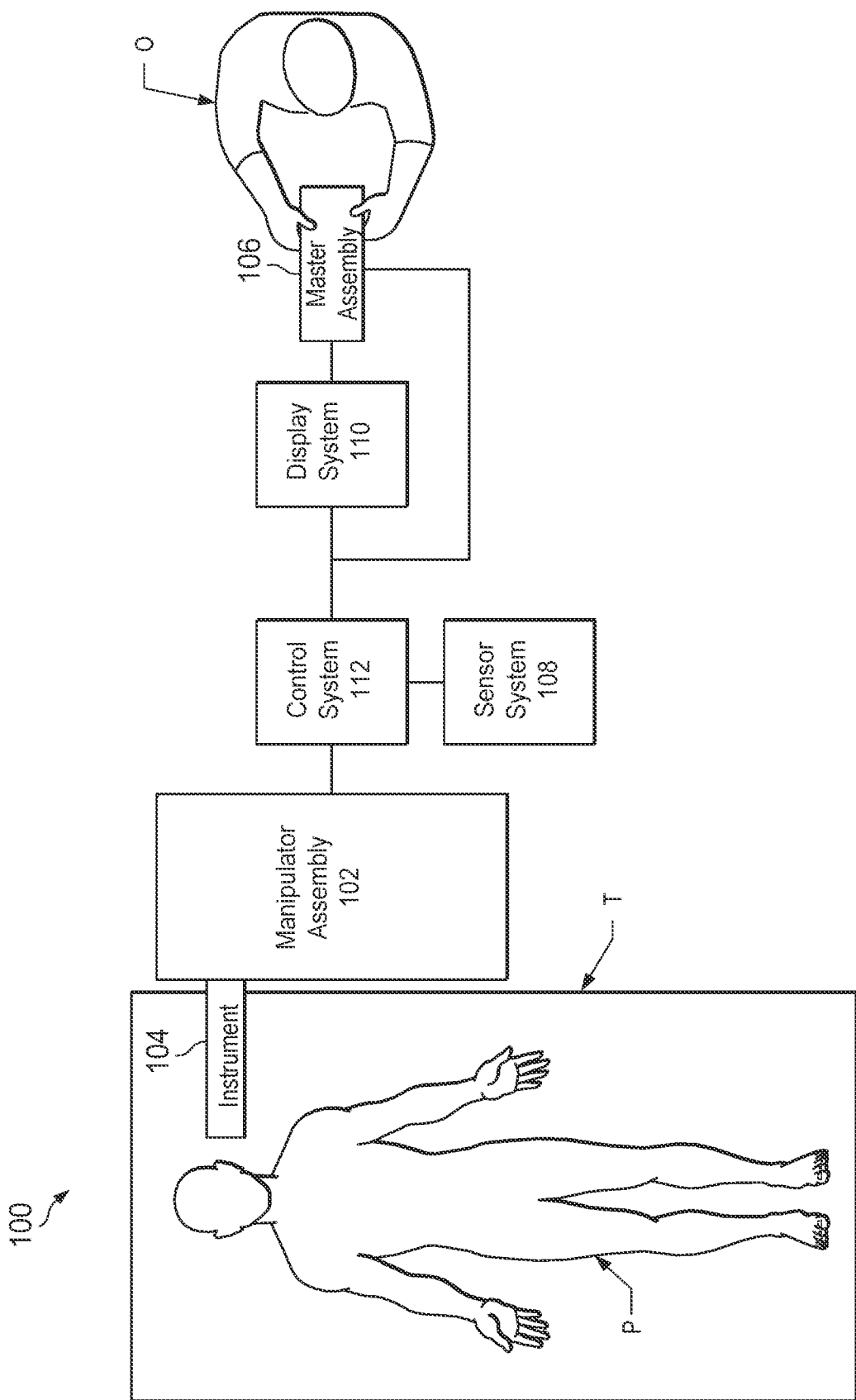
FIG. 1 is a simplified diagram of a teleoperated medical system, in accordance with embodiments of the present disclosure.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. An operator input system called a master assembly 106 allows an operator O (e.g., a surgeon, a clinician, or a physician) as illustrated in FIG. 1 to view the interventional site and to control teleoperational manipulator assembly 102.

Master assembly 106 may be located at a physician's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112. The processors of the control system 112 may execute instructions corresponding to methods and operators described herein.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter the data points. In some embodiments, a virtual navigational image may be presented in the display 110 that depicts a model of an anatomical passageway from a perspective of an instrument being inserted along or through a corresponding actual anatomical passageway.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. The optical fiber of the shape sensor system 222 may enable the simultaneous collection of a set of measured points that describe the positions of various portions of the shape sensor 222 along the length of the flexible catheter body 216 at a single point in time. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties.

Sensors in some embodiments may employ other suitable strain sensing techniques, such as Rayleigh scattering, Raman scattering, Brillouin scattering, and fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor 222 may also function as the position sensor because the shape of the sensor 222 together with information about the location of the base of the shape sensor 222 (in the fixed coordinate system of the patient, referred to as "patient space") allows the location of various points along the shape sensor, including the distal tip, to be calculated.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static. The tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the track, which may be linear or curved, of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position Lx may further be used as an indicator of the distance or insertion depth to which distal end 318 of elongate device 310 is inserted into the passageways of the anatomy of patient P. During insertion and while inserted within the anatomy of the patient P, the shape sensor 314 may be used to collect measured data points within the anatomy of the patient P.

Embodiments of the point gathering instrument 304 may collect measured points using any number of modalities, including EM sensing and shape-sensing. As the measurement points are collected from within the anatomic passageways of a patient, the points are stored in a data storage device, such as a memory. The set of measured points may be stored in a database that includes at least some, but may include all, of the measured points obtained during the procedure or immediately before the procedure. The set of measured points may be binned, sorted, or filtered, to produce subsets of measured points that are related in some way, such as being obtained during a common phase or portion of a phase of a periodic physiological motion, such as respiration. As stored in memory, each of the points may be represented by data comprising coordinates of the point, a timestamp, and a relative sensor position or individual sensor ID (when multiple sensors distributed along a length of the point gathering instrument 304 are used to determine the location of several points simultaneously). The binned subsets of measured points may be stored in separate data structures and/or in separate portions of memory. In some embodiments, data representing each point may also include a respiratory phase marker that indicates the respiratory phase of the patient in which the point was collected. A patient movement tracker 322 may be used to monitor and detect movement of the patient P. This movement may include gross movements as well as periodic physiological movements, such as respiration. Accordingly, the movement tracker 322 may serve as a physiological phase detector. The movement tracker 322 may be an optical tracking system or any other suitable system. In other embodiments, respiration may be monitored by a ventilator or by any other technique.

FIGS. 4A, 4B, 4C, and 4D illustrate the advancement of the catheter 310 of FIGS. 3A and 3B through anatomic passageways 402 of the lungs 400 of the patient P of FIGS. 1 and 3. These passageways 402 include the trachea and the bronchial tubes. As the catheter 310 is advanced as the carriage 306 moves along the insertion stage 308, the surgeon S may steer the distal end 318 of the catheter 310 to navigate through the anatomic passageways 402. In navigating through the anatomic passageways 402, the catheter 310 assumes a shape that may be "read" by the shape sensor 314 extending within the catheter 310. As described herein, measured points obtained using the flexible catheter 310 may be assigned to one or more bins based on a variety of factors. For example, the measured points may be assigned to bins that correspond to portions of a periodic physiological motion, such as respiration. The measured points may also be assigned to bins that correspond to an insertion depth of the catheter 310, such that points measured within the trachea, or a particular generation of the bronchial passageways, may be pooled or included in a single bin even as the distal end 318 of the catheter 310 advances through the anatomic passageways 402.

FIG. 5 is a flowchart illustrating a general method 500 for use in an image-guided surgical procedure. At a process 502, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 400 of FIGS. 4A-D. At a process 504, a computer system either operating alone or in combination with manual input is used to convert the recorded images into a segmented two-dimensional or three-dimensional composite representation or model of a partial or an entire anatomic organ or anatomic region. For example, FIG. 6A illustrates a segmented model 600 of the lungs 400 of FIGS. 4A-D. Due to naturally occurring limitations or to limitations set by an operator, the segmented model 600 may not include all of the passageways present within the human lungs, but includes some passageways 601. For example, relatively narrow and/or distal passageways of the lungs may not be fully included in the segmented model 600. The segmented model 600 may be a three-dimensional model, such as a mesh model or another suitable model, that includes the walls defining the interior lumens or passageways of the lungs. In general, the model provides a mechanism or means for distinguishing between points within a region of anatomy and points outside the region of anatomy. The composite representation and the image data set describe the various locations and shapes of the passageways and their connectivity and may omit undesired portions of the anatomy included in the pre-operative or intra-operative image data. In some embodiments, the model 600 may include specifically desired features, such as a suspected tumor or other tissue portion of interest.

During the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image, like the model 600. To represent the model, the segmentation process may delineate sets of voxels representing the target anatomy and then apply a function, such as marching cube function, to generate a 3D surface that encloses the voxels. The model may be made by generating a mesh, volume, or voxel map. This model may be shown in the display 110 to aid the surgeon S in visualizing the anatomy, such as the interior passageways of the lungs.

Additionally or alternatively, the model may include a centerline model that includes a set of interconnected line segments or points extending through the centers of the modeled passageways. FIG. 6B shows an exemplary centerline model 602 derived from the model 600 or directly from the imaging data. The centerline segmented model 602 may include a set of three-dimensional straight lines or a set of curved lines that correspond to the approximate center of the passageways contained in the segmented model 602. The higher the resolution of the model, the more accurately the set of straight or curved lines will correspond to the center of the passageways. Representing the lungs with the centerline segmented model 602 may provide a smaller set of data that is more efficiently processed by one or more processors or processing cores than the data set of the segmented model 602, which represents the walls of the passageways of model 600. In this way the functioning of the control system 112 may be improved.

As shown in FIG. 6B, the centerline segmented model 602 includes several branch points, some of which are highlighted for visibility in FIG. 6B. The branch points A, B, C, D, and E are shown at each of several of the branch points. The branch point A may represent the point in the model at which the trachea divides into the left and right principal bronchi. The right principal bronchus may be identified in the centerline segment model 602 as being located between branch points A and B. Similarly, secondary bronchi are identified by the branch points B and C and between the branch points B and E. Another generation may be defined between branch points C and D. Each of these generations may be associated with a representation of the diameter of the lumen of the corresponding passageway. In some embodiments, the model 602 may include an average diameter value of each segmented generation. The average diameter value may be a patient-specific value or a more general value derived from multiple patients.

Where the model includes a centerline model including a set of interconnected line segments, those line segments may be converted to a cloud or set of points 604, referred to as model points, which are represented by the dashed lines of FIG. 6C. By converting the line segments into points, a desired quantity of model points corresponding to the interconnected line segments can be selected manually or automatically to represent the centerline model 602 (and thereby the model 600) during a registration process. In data, each of the points of the set of model points 604 may include coordinates such as a set of XM, YM, and ZM, coordinates, or other coordinates that identify the location of each point in the three-dimensional model space. In some embodiments, each of the points may include a generation identifier that identifies which passageway generation the points are associated with and/or a diameter or radius value associated with that portion of the centerline segmented model 602. In some embodiments, information describing the radius or diameter associated with a given point may be provided as part of a separate data set.

After the centerline segmented model 602 is generated and stored in data as the set of points 604 shown in FIG. 6C, the model points 604 may be retrieved from data storage for use in an image-guided surgical procedure. In order to use the centerline segmented model 602 and the model 600 in the image-guided surgical procedure, the model points 604 may be registered to associate the modeled passageways in the model 600 with the patient's actual anatomy as present in a surgical environment.

Returning to FIG. 5, at a process 506, measured points may be obtained from patient anatomy that corresponds to the anatomical model, as shown in FIGS. 3A-B and 4A-D. At a process 508, the anatomic model data is registered to the patient anatomy prior to and/or during the course of an image-guided surgical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique, or another point set registration methods may also be used in registration processes within the scope of this disclosure.

After the process 508 in which the anatomical model is registered to the patient anatomy so that medical instrument positioned with respect to the patient anatomy can b e represented with respect to the anatomical model, the collection of measured points from the patient anatomy may continue. As new measured points are added, the registration may be updated at a process 510. The updating of the registration may be performed continuously throughout a surgical procedure. In this way, changes due to patient movements (both gross movements and periodic physiological movements) may be compensated for. Additionally, measured points may be assigned into various subsets of points by one or more criteria, and by which some subsets or a particular subset may be determined to be better than others in registering the patient anatomy to the anatomical model. Points may also be assigned a numeric weighting reflecting the partial probability that the point is correctly assigned to any subset of point. However, a subset that may have provided optimal registration for a first period of time may become suboptimal at a later period of time. Updating the registration to use whichever subset of measured points provides the optimal registration at the time, may ensure the best and most useful relationship between the model and the anatomy is maintained. When a statistically significant change in the quality of a registration occurs (e.g., there is a significant change in the error value associated with the registration), the subset of measured points associated with that registration may be emptied by deletion of all points or may have a weighting of measured points applied thereto.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. Some embodiments of the systems and methods described herein perform registration based upon ICP, or another point set registration algorithm, and the calibrated movement of a point gathering instrument with a fiber optic shape sensor, thus eliminating or minimizing disruptions in the surgical environment. Other registration techniques may be used to register a set of measured points to a pre-operative model or a model obtained using another modality. In the embodiments described below, EM sensors on the patient and the instrument and optical tracking systems for the instrument may be eliminated.

FIG. 7 is a flowchart illustrating a method 700 used to provide guidance to a clinician in an image-guided surgical procedure on the patient P in the surgical environment 300, according to some embodiments of the present disclosure. The method 700 is illustrated in FIG. 7 as a set of blocks, steps, operations, or processes. Not all of the illustrated, enumerated operations may be performed in all embodiments of the method 700. Additionally, some additional operations that are not expressly illustrated in FIG. 7 may be included before, after, in between, or as part of the enumerated operations. Some embodiments of the method 700 may include machine-readable instructions corresponding to the operations of the method 700 and stored in a memory. These instructions may be executed by a processor like a processor of the control system 112.

Thus, some embodiments of the method 700 may begin at an operation 702, in which the set of measured points is collected along the length of a catheter or other medical instrument. For example, the catheter may be the point gathering instrument 304 of FIGS. 3A and 3B, or the medical instrument system 200 of FIG. 2. The catheter may include a fiber optic shape sensor that may be used to generate a plurality of three-dimensional points representing the shape of the catheter. Three-dimensional points may be related to a patient space by having a proximal end of the fiber optic shape sensor and a known location or a detected location.

In practice, the distal end 318 of the catheter 310 may traverse the patient P's anatomic passageways (e.g., airways of the patient's lungs) recording, via data from the shape sensor 314, location data for the distal end of the catheter and other points along the shape of the shape sensor. This location data may include, or be processed to obtain, a set of measured points as described herein. More specifically, the movement of the distal tip of the catheter 610 may be controlled via teleoperational, manual, or automated control (e.g., via master assembly 106) to survey a portion of the anatomic passageways.

For example, teleoperational control signals may cause the carriage 306 to move along the axis A, causing the distal end 318 of the catheter to advance or retract within the anatomic passageways. Also or alternatively, teleoperational control signals may cause actuation of control members extending within the surgical instrument to move the distal end 318 in a range of movements including yaw, pitch, and roll. As the catheter is moved within the plurality of passageways, shape sensor data (and/or other position data in other embodiments that do not include a shape sensor) is gathered for multiple locations of the distal tip. In some embodiments, the catheter may extend up to approximately three branches deep into the various passageways. In some embodiments, the catheter may be extended through or into approximately three or more branched generations on each side of the lung. The number of generations accessible with the catheter 310 may increase as the diameter of the flexible catheter 310 decreases and/or the flexibility of the flexible catheter 310 increases.

In some embodiments, a calibration procedure may be performed prior to the collection of measured points using a position measuring device like the point gathering instrument 304 or another suitable device, a relative position and/or orientation of a sensor reference point along an insertion path. For example, the point gathering instrument 304 of FIGS. 3A and 3B may be used to determine a position and orientation of the point 316 as the carriage 306 moves from a retracted position with the point 316 at location $L_0$ to an advanced position with the point 316 at the location $L_1$. The calibration procedure may determine the direction of the movement of the point 316 for each change in the position measuring device 320. For example, the distal end 318 of the catheter 310 may be held in a fixed position while the instrument body is routed along the insertion stage 308. The position and orientation data collected by the shape sensor from the fixed point 316 is correlated with the position measuring device data as the instrument body is routed along the insertion stage, thus calibrating movement of the point 316 along the axis A of the insertion stage 308.

Optionally, in an operation 703, a state input may be received by the control system 112. For example, the state input may be a periodic physiological motion signal describing the respiration of patient P or heartbeats of patient P. Other periodic physiological motion signal may be received and used in other embodiments. FIGS. 8A and 8B, discussed in more detail further below illustrate a single period of an exemplary periodic physiological motion signal 800. The periodic physiological motion signal includes a period T shown along the x-axis and amplitude shown along the y-axis. The signal shown in FIGS. 8A and 8B is simplified to more clearly communicate certain aspects of the present disclosure. Other state inputs may include non-physiological inputs such as instrument velocity, force, applied strain, or orientation. Other state inputs may include a detected obstruction (e.g., due to fog or debris) of the camera. Other state inputs may include a tagged measured point that is designated as belonging at a particular anatomical location or within a particular anatomic passageway. Such a tagged point may serve as a "ground truth" point during a registration.

At an operation 704, the measured points may be assigned to a plurality of subsets of measured points. In some embodiments, the operations 702 and 704 may be performed substantially simultaneously. In other embodiments, the operation 702 may include storing the set of measured points in a pool of points in memory and the operation 704 may include retrieving the set of measured points from memory and then assigning the retrieved points to the plurality of subsets. The assignment of measured points to subsets may be referred to herein as "binning." The measured points may each be assigned to one of several bins. The bins may be data structures and/or specific portions of memory. FIGS. 8A and 8B illustrate some exemplary ways in which measured points may be assigned to particular bins. Assignment of each point to any bin may be binary (explicitly inside or outside a given bin) or it may contain a soft assignment to any bin represented by some fractional weighting.

As shown in FIG. 8A, the periodic physiological motion signal 800 may be used to bin collected measured points. FIG. 8A illustrates time-based or period-based binning, in which the time at which a particular measured point is obtained indicates the bin to which the point should be assigned. It should be noted that, when a fiber optic shape sensor is used to collect the measured points that a plurality of points are collected at a single time. All of the points collected from the fiber optic shape sensor at that time may be assigned to the same bin or subset of points. For example, if points are collected from the fiber-optic sensor 314 at a time in between zero and $\frac{1}{8}^{th}$ of T, the points may be assigned to bin A. If the points are collected at a time between $\frac{1}{8}^{th}$ of T and $\frac{3}{8}^{th}$ of T, the points may be assigned to bin B. If the points are collected at the time between $\frac{3}{8}^{th}$ of T and $\frac{5}{8}^{th}$ of T, the points may be assigned to bin C. If the points are collected at a time between $\frac{5}{8}^{th}$ of T and $\frac{7}{8}^{th}$ of T, the points may be assigned to bin D. If the points are collected at a time between $\frac{7}{8}^{th}$ of T and T, the points may be assigned to bin A. Other embodiments of the operation 704 may assign collected points to a bin differently. For example, the measured points may be assigned to one of more than four bins. The bins may be associated with unequal portions of the period T. The cutoffs for the bins may occur at the peak and the trough of the signal 800.

As shown in FIG. 8A, the periodic physiological motion signal 800 may be used to bin measured points according to the amplitude of the signal 800. FIG. 8B illustrates amplitude cutoffs that sort the measured points into three bins: bin E, bin F, and bin G. For example, points collected when the amplitude of the periodic physiological motion signal 800 is greater than half a peak value may be assigned to bin E. Points collected when the amplitude of the periodic physiological motion signal 800 is less than half a minimum value may be assigned to bin G. Points collected in between these amplitude values may be assigned to bin F. Other embodiments may include more bins or fewer bins.

Referring now to FIG. 9, shown therein is an exemplary illustration of operation 704 of the method 700. FIG. 9 depicts the catheter 310 of FIGS. 3A-B and 4A-D. A shape sensor disposed within the catheter 310 (i.e., the shape sensor 314) measures points during four discrete time portions (at times $t_1$, $t_2$, $t_3$, and $t_4$) within a period T. The times $t_1$, $t_2$, $t_3$, and $t_4$ correspond to different bins, like the bins A, B, C, and D as shown in FIG. 9. As shown in FIG. 9, the shape and position of the catheter 310 at $t_4$ is different from the shape and position of the catheter 310 at the times $t_1$, $t_2$, and $t_3$. This difference is not due to insertion of the catheter 310 deeper into the anatomic passageways 402, but instead may be due to the periodic physiological motion of the lung 400 during respiration by the patient P.

Figure 10A:
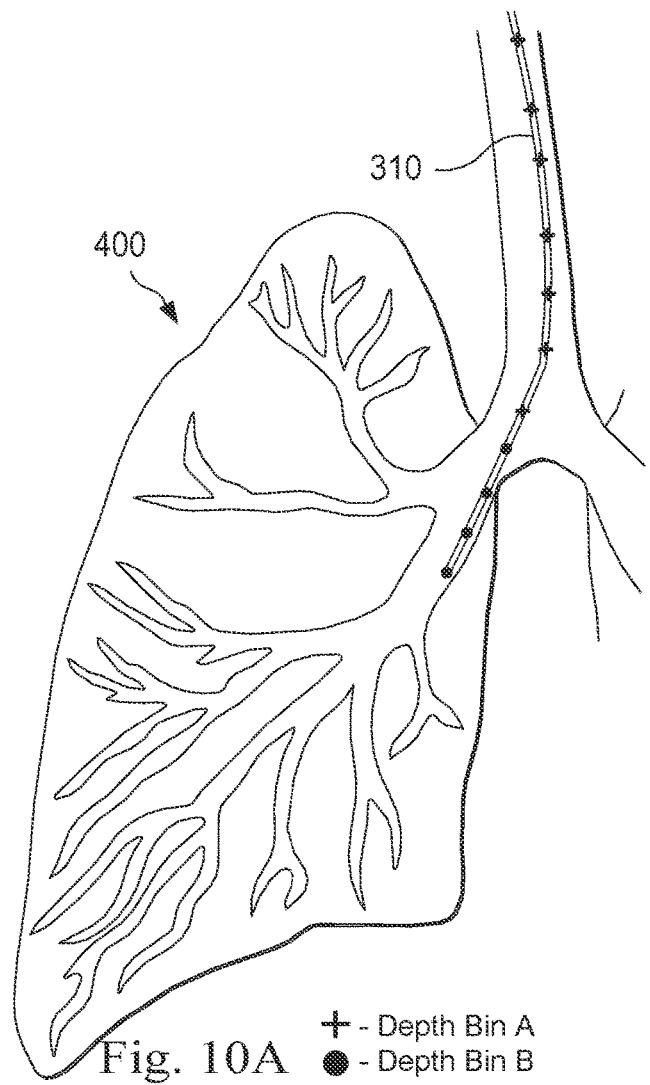
Figure 10B:
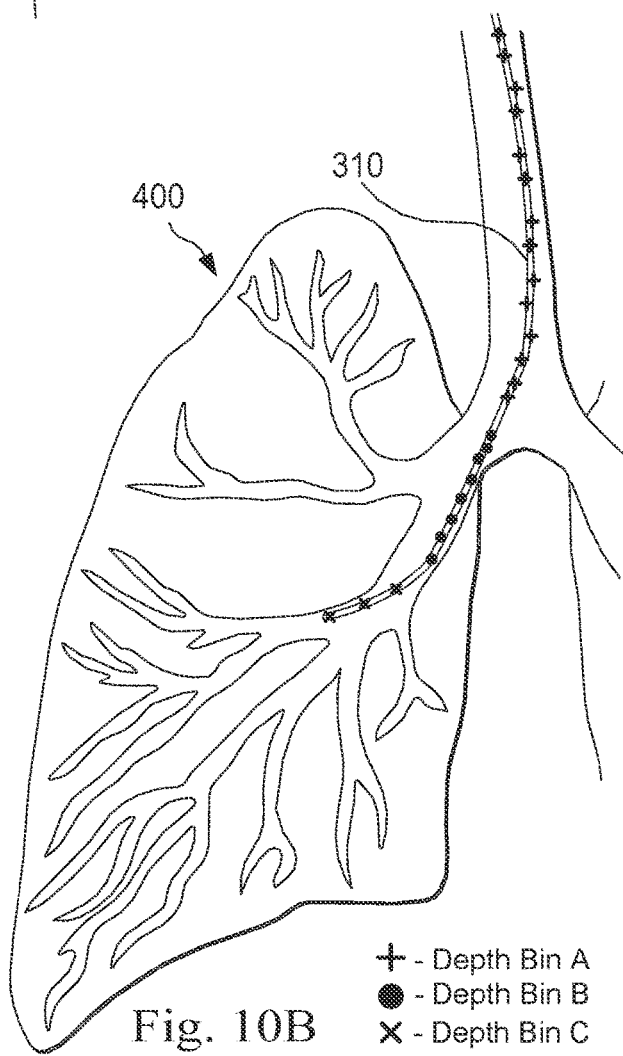
Figure 10C:
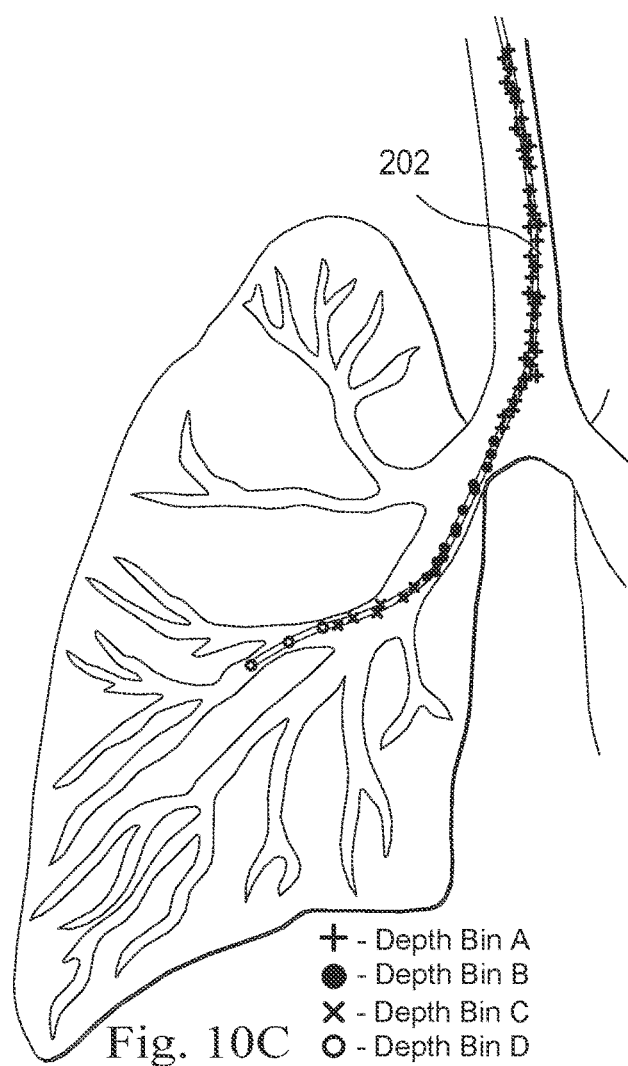
Figure 10D:
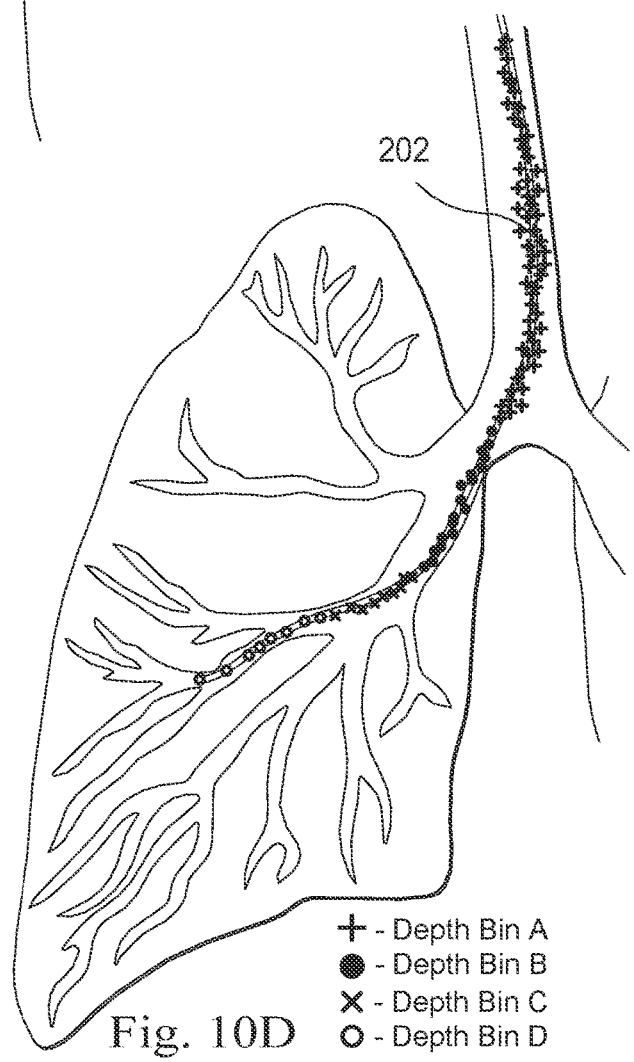

Referring now to FIGS. 10A, 10B, 10C, and 10D, another embodiment of the operation 704 is shown. In assigning each of the measured points to one of a plurality of bins, the assignment may be made based on an insertion depth of the catheter used to measure the points. Accordingly, a depth value may be received based on the movement of the carriage 306 relative to the stage 308 from an encoder or another sensor. The cutoffs between depths may be determined preoperatively based upon the segmented centerline model 602 of FIG. 6B. Other depths may be used in other embodiments. As shown in FIG. 10A, the points collected at a specific time by the catheter 310 may be sorted or assigned into depth bins A and B. In FIG. 10B, the catheter 310 has been inserted more when the measured points are collected and so the points are assigned to three depth bins: depth bins A, B, and C. As shown in FIGS. 10C and 10D, as the catheter 310 is inserted deeper into the anatomical passageways of a lung 400, measured points are assigned to depth bins A, B, C, and D. As shown in FIGS. 10A-D, the more proximal depth bins may include more measured points because a portion of the catheter 310 has been in proximal depths for a longer period of time, during which points may be collected on a regular basis. In some embodiments the number of points in a bin may be capped such that as new points are measured, the oldest points are removed from the subset or pool of points associated with that bin.

Returning again to FIG. 7 and the method 700, at operation 705, a set of model points from a model may be received by the control system 112. For example, the set of model points may be a set of points representing a model of the lung 400. The set of model points received at operation 705 may be similar to the model points 604 of FIG. 6C, which are a set of points derived from the centerline model 602, which was based on the model 600. The set of model points 604 may be used to register the model 600 to the set of measured points collected with the catheter 310.

After the operation 704, an initial seed transformation may be performed at operation 706 to roughly place the measured points in relation to the model points, such that subsequent iterative registration operations can be performed. The registration process may be seeded with known information about the displacement and orientation relationship between the patient surgical environment and the anatomic model. For example, landmarks associated with the main carinas in the lungs 400 may be identified in the anatomic model information. Corresponding locations may be included in the measured points as part of the work flow. At operation 707, the control system 112 may register each subset of measured points to the set of model points. Registration may be accomplished using a point set registration algorithm such as an iterative closest point (ICP) technique as described in operations 708-714, or by implementation of another registration algorithm.

At an operation 708, after the initial coarse seed transformation has been performed to initiate the registration process, the set of measured data points D gathered from within the patient P is matched to the anatomic model points 604. For example, each of the measured data points D may be matched with the closest point in the set of anatomic model points 604. In this embodiment, the anatomic model points 604 is a set of points along the centerlines generated from a three-dimensional anatomic model, like the segmented centerline model 602 is generated from the segmented model 600 of FIGS. 6A and 6B. The registration algorithm identifies matches between closest points in the measured data points and in the set of anatomic model points 604. A result may be seen in FIG. 11A, which shown the model points 604 with a set of measured points 1100 after an initial seeding or registration process has begun. As illustrated in FIG. 11A, the set of measured points 1100 includes four subsets of measured points including the subset 1102A (represented by solid circles), the subset 1102B (represented by plus signs), the subset 1102C (represented by open circles), and the subset 1102D (represented by x's). The subsets 1102A, 1102B, 1102C, and 1102D may be collectively referred to as subsets 1102.

In various alternatives, matching between the model points 604 and each of the subsets 1102 may be accomplished by using brute force techniques, KD tree techniques, etc. Some matches may be discarded based on maximum distance threshold calculations, maximum angle threshold calculations, or other metrics employed to filter out matches that are not deemed to be reliable enough for inclusion in the model. The anatomic model points 604 may be represented by any of several different kinds of points, including centerline points, mesh points, and/or volume points.

Referring again to the method 700 of FIG. 7, at an operation 710, the transformation needed to map each subset of subsets 1102 to the position and orientation of the matched anatomic model points 604 is determined. More specifically, an overall computed offset in position and orientation is determined for each of subsets 1102. In some embodiments, the computed corrective transformation may be limited such that only a certain number of degrees of rotation or a certain number of millimeters of displacement may be applied in a single iteration of the process. For example, even if a rotation or reorientation of the anatomic model points 604 of 20° is computed, the medical system may limit the change in orientation to 10°, 5°, or less. Similarly, in some embodiments even if a displacement of 40 mm is computed, the control system 112 may limit the displacement available in a single iteration to 20 mm, 10 mm, 5 mm, or less. In some embodiments, the limits may change according to a number of iterations performed such that less movement is permitted in later iterations than in earlier iterations.

At an operation 712, each subset 1102 may be transformed using a rigid or non-rigid transformation that applies the computed offset in displacement and orientation to specifically move each point in the particular subset 1102. In an alternative embodiment, the modeled data points may be transformed by using a rigid or non-rigid transform that applies the computed offset in displacement and orientation to move each point in the set of model points 604 toward the subsets 1102. Accordingly, some embodiments of the present disclosure may refer to registering measured points to model points and moving (including translating and/or changing the orientation of) the measured points to better align with the model points, bringing them into a common space or common frame of reference. These registrations may be understood as registration candidates. In order to register the model 600 with the measured points 1100, bringing the model 600 into patient space, an optimal registration candidate may be identified and selected.

At an operation 714, the registration error between each of the subsets 1102 and the matched anatomic model points 604 is evaluated. In some embodiments, the error may be computed as the cumulative error or distance between each measured point to its nearest model point after being transformed. Alternatively, there might be expressed as the change in orientation and displacement from a previously computed registration. This may include the calculation of error values, including error values for orientation and displacement for each of the subsets 1102. In other words, error factors for orientation and displacement may be individually determined for each matched subset 1102. If the error factors in aggregate are greater than a threshold value, additional iterations of operations 708-714 may be repeated until the overall position and orientation error factors falls below the threshold value.

At an operation 716, the convergence of each of the subsets 1102 may be compared to determine which of the registration candidates is optimal for use in a procedure relying upon the model 600 of FIG. 6A. In other words, overall error values associated with the registration candidates of each of the subsets 1102A, 1102B, 1102C, and 1102D to the model points 604 may be compared. The registration candidate having the smallest overall error value may be used to bring the model points 604 into the patient space in which the points 1100 are collected. The association between the model points 604 may permit the model 600 to be expressed in the patient space. In some embodiments, after determining the convergence of each subset, the convergence value may be compared with a threshold and, if the convergence drops below the threshold or if the associated error exceeds the threshold, the points collected up until that point in the failing subset or subsets may be discarded. For example, when the patient P makes a gross movement, the error for the registrations associated with one or more of the subsets may include significant errors, making the registration unusable for image-guided surgery. Because the subset has been "contaminated" with bad data associated with the patient P's movement, the subset may be emptied and point collection make begin anew.

For example, at operation 718, a visual representation of the optimal registration of the model points 604 (and thereby the model 600) may be displayed in a graphical user interface provided by the display 110 of FIG. 1. The visual representation may depict the medical instrument system 200 in relation to the model 600. An exemplary visual representation is shown in FIG. 13A. FIG. 13A illustrates a display 1300 displaying, in a user interface, a rendering of anatomic passageways of a human lung based upon anatomic model 600 of FIG. 6A. With the model space registered to the patient as described above in FIG. 7, the current shape of the catheter 310 and the location of the distal end 318 may be located and displayed concurrently with the rendering of the passageways 601, which includes passageways 601A and 601B. The data points may be visually represented in a user interface by a plurality of points or dots on the display or as a rendered model, such as a mesh or wire model created based on the set of data points. In some embodiments, a visual representation may be refreshed in the display 110 after each processing operations has been implemented to alter the data points. FIG. 13B illustrates another exemplary display 1350 of a visual representation that may be provided to the surgeon S to aid in guiding the surgery. FIG. 13B shows an internal view of a portion of the model 600 from a perspective of the medical instrument 200, and depicts rendered models of the passageways 601A and 601B. The model 600 may be rendered in two or three-dimensions to facilitate guidance of the surgery.

The principles and embodiments of the present disclosure may improve image guided surgery by improving registration between models of patient anatomy and medical instruments being manipulated within the patient anatomy during a surgical procedure. Multiple candidate registrations may be produced based on subsets of measured data points and the multiple registrations may be compared to determine an optimal registration to be applied to the model to bring it into the patient space. These multiple candidate registrations may be continuously updated and compared to each other and to threshold values to ensure that the highest fidelity registration at any given time as provided for use in image guided surgery.

In some embodiments, when a later registration replaces an earlier registration or an earlier registration is deemed replaceable by the control system 112 with a later registration, an alert may be provided to the clinician through a user interface to indicate that there is a change in registration (e.g., from one subset of measured points to another) or that there is a superior registration available. In some embodiments, the control system 112 may require clinician approval through the user interface before the superior registration is implemented. For example, when a superior registration is identified an alert may be rendered to the display 110 along with a button or other user interface element by which the clinician can approve or disapprove to the new registration. The new registration will then be implemented or not depending on the clinician's decision.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, collecting, assigning, detecting, initiating, registered, displaying, receiving, generating, determining, moving data points, segmenting, matching, etc. may be performed at least in part by the control system 112 or the processor thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
    collecting a set of measured points along a flexible catheter as the flexible catheter is inserted into one or more anatomic passageways of a patient, the measured points based on a shape of the flexible catheter in a patient space;
    assigning each measured point of the set of measured points to a respective subset of a plurality of subsets of measured points based upon a depth of each measured point within the one or more anatomic passageways;
    comparing the plurality of subsets to identify an optimal subset of the plurality of subsets; and
    registering a model of the one or more anatomic passageways to the patient space based on a set of model points of the model and the optimal subset.

2. The method of claim 1, wherein a number of subsets in the plurality of subsets of measured points is based upon an insertion depth of the flexible catheter into the one or more anatomic passageways such that the number of subsets increases as the flexible catheter is advanced distally.

3. The method of claim 2, wherein the insertion depth is determined by measuring movement of an instrument carriage to which the flexible catheter is attached relative to an insertion stage.

4. The method of claim 1, further comprising assigning a numeric weighting to each point of the set of measured points, wherein the numeric weighting is utilized during the comparing the plurality of subsets to identify the optimal subset.

5. The method of claim 4, wherein the numeric weighting of a respective point reflects a probability that the respective point is correctly assigned to its respective subset.

6. The method of claim 1, further comprising:
    updating the plurality of subsets by removing at least a portion of the measured points from at least one subset of the plurality of subsets.

7. The method of claim 1, wherein the comparing the plurality of subsets to identify the optimal subset of the plurality of subsets comprises:
    determining a convergence value of each subset of the plurality of subsets relative to the set of model points.

8. The method of claim 7, further comprising:
    deleting all measured points from at least one subset of the plurality of subsets, after determining the convergence value of each subset, based on comparing the convergence value associated with the at least one subset to a threshold value.

9. The method of claim 1, further comprising:
    updating at least one subset of the plurality of subsets by discarding an oldest measured point from the at least one subset based on a new measured point being assigned to the at least one subset.

10. The method of claim 1, wherein collecting the set of measured points comprises interrogating a shape sensor of the flexible catheter.

11. The method of claim 1, further comprising displaying a visual representation of the registered model in a user interface provided by a display.

12. The method of claim 1, wherein each subset of the plurality of subsets is associated with a range of insertion depths, the range of insertion depths associated with each subset being determined based on the model.

13. The method of claim 1, wherein the registering the model to the patient space based on the set of model points and the optimal subset comprises translating the set of model points from a model space to the patient space or translating the measured points of the optimal subset from the patient space to the model space.

14. A medical instrument system comprising:
    a flexible catheter;
    a point gathering instrument extending along a length of the flexible catheter and configured to collect a set of measured points; and
    a tracking system configured to perform operations comprising:
        collecting the set of measured points as the flexible catheter is inserted into one or more anatomic passageways of a patient, the measured points based on a shape of the flexible catheter in a patient space;
        assigning each measured point of the set of measured points to a respective subset of a plurality of subsets of measured points based upon a depth of each measured point within the one or more anatomic passageways;
        comparing the plurality of subsets to identify an optimal subset of the plurality of subsets; and
        registering a model of the one or more anatomic passageways to the patient space based on a set of model points of the model and the optimal subset.

15. The medical instrument system of claim 14, further comprising:
    an instrument carriage to which the flexible catheter is attached;
    an insertion stage upon which the instrument carriage is movable; and
    a position measuring device configured to measure a position of the instrument carriage relative to the insertion stage, wherein a number of subsets in the plurality of subsets of measured points is based upon an insertion depth of the flexible catheter into the one or more anatomic passageways based on the position of the instrument carriage measured by the position measuring device such that the number of subsets increases as the flexible catheter is advanced distally.

16. The medical instrument system of claim 14, wherein the tracking system is further configured to perform:
    assigning a numeric weighting to each measured point of the set of measured points, wherein the numeric weighting is utilized during the comparing the plurality of subsets to identify the optimal subset.

17. The medical instrument system of claim 16, wherein the numeric weighting of each measured point of the set of measured points reflects a probability that each respective measured point is correctly assigned to its respective subset of the plurality of subsets.

18. The medical instrument system of claim 14, wherein the tracking system is further configured to perform:
    updating the plurality of subsets by removing at least a portion of the measured points from at least one subset of the plurality of subsets.

19. The medical instrument system of claim 14, wherein the tracking system is configured to perform the comparing the plurality of subsets to identify the optimal subset of the plurality of subsets by:
    determining a convergence value of each subset of the plurality of subsets relative to the set of model points.

20. The medical instrument system of claim 19, wherein the tracking system is further configured to perform:
    deleting all measured points from at least one subset of the plurality of subsets, after determining the convergence value of each subset, based on comparing the convergence value associated with the at least one subset to a threshold value.

* * * * *

UNITED STATES PATENT AND TRADEMARK OFFICE
CERTIFICATE OF CORRECTION

PATENT NO. : 11,864,856 B2
APPLICATION NO. : 18/154710
DATED : January 9, 2024
INVENTOR(S) : Timothy D. Soper and Vincent Duindam It is certified that error appears in the above-identified patent and that said Letters Patent is hereby corrected as shown below:

In the Specification

Column 1, Line 16, delete "is"

Column 1, Line 17, delete "its"

Column 6, Line 11, change "(MM)" to -- (MRI) --

Column 16, Line 5, change "b e" to -- be --

Signed and Sealed this
Twenty-seventh Day of February, 2024

Katherine Kelly Vidal
*Director of the United States Patent and Trademark Office*